United States Patent
Laaksonen et al.

(10) Patent No.: US 11,602,643 B2
(45) Date of Patent: Mar. 14, 2023

(54) SYSTEMS AND METHODS FOR COMBINING CLINICAL GOALS WITH KNOWLEDGE BASED DOSE PREDICTION IN TREATMENT PLANNING

(71) Applicant: Varian Medical Systems International AG, Steinhausen (CH)

(72) Inventors: Hannu Mikael Laaksonen, Espoo (FI); Esa Kuusela, Helsinki (FI); Maria Isabel Cordero Marcos, Espoo (FI); Jarkko Peltola, Tuusula (FI)

(73) Assignee: VARIAN MEDICAL SYSTEMS INTERNATIONAL AG, Steinhausen (CH)

( * ) Notice: Subject to any disclaimer, the term of this patent is extended or adjusted under 35 U.S.C. 154(b) by 934 days.

(21) Appl. No.: 16/237,496

(22) Filed: Dec. 31, 2018

(65) Prior Publication Data
US 2020/0206533 A1    Jul. 2, 2020

(51) Int. Cl.
*G06F 9/44* (2018.01)
*A61N 5/10* (2006.01)
*G06N 20/00* (2019.01)
*G06N 7/00* (2023.01)

(52) U.S. Cl.
CPC .......... *A61N 5/1031* (2013.01); *G06N 7/005* (2013.01); *G06N 20/00* (2019.01); *A61N 2005/1034* (2013.01)

(58) Field of Classification Search
CPC .................................................. A61N 5/1031
USPC .......................................................... 703/13
See application file for complete search history.

(56) References Cited

U.S. PATENT DOCUMENTS

| 6,888,919 B2 | 5/2005 | Graf |
| 7,649,981 B2 | 1/2010 | Seppi et al. |
| 2016/0140300 A1* | 5/2016 | Purdie ............... G16H 10/60 705/2 |

* cited by examiner

*Primary Examiner* — Timothy A Mudrick
(74) *Attorney, Agent, or Firm* — Harness, Dickey & Pierce, P.L.C.

(57) ABSTRACT

A treatment planning apparatus includes: a modeler configured to obtain a model definition, wherein the model definition comprises a first quality metric of a first clinical goal; and a treatment planner having: a model trainer configured to obtain a set of existing treatment plans following desired clinical practice, and to perform model training to obtain a trained model based on the existing treatment plans and the first quality metric of the first clinical goal; an objective generator configured to generate a cost function based on the trained model; and an optimizer configured to determine a treatment plan based on the cost function.

20 Claims, 5 Drawing Sheets

SYSTEMS AND METHODS FOR COMBINING CLINICAL GOALS WITH KNOWLEDGE BASED DOSE PREDICTION IN TREATMENT PLANNING

FIELD

This application relates generally to radiation therapy, and more specifically, to radiation treatment planning for radiation therapy.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. During a radiation planning session, radiation treatment planning is performed before treatment radiation is delivered to a patient. This allows an accurate and precise dosage of radiation to be delivered to a patient. Embodiments of methods and systems for determining treatment plans are described herein.

SUMMARY

In inverse treatment planning optimization, used for example in intensity modulated treatment planning (IMRT), an optimizer is provided. The optimizer performs treatment plan optimization based on a defined mathematical cost function, and the optimal solution is the plan that minimizes that cost function. Presenting clinical goals as a cost function may be a demanding task. The cost function may be generated based on two separate approaches.

In the knowledge based approach, a user may define a set of plans following desired clinical practice (without defining the clinical goals directly). Machine learning techniques may then be used to create a statistical model that will transfer this clinical practice into a new patient geometry. The cost function may then be generated based on the new patient geometry.

In the direct clinical goal approach, the user may directly define a prioritized list of goals. A treatment planning optimizer may then consider different cost function definitions until a cost function is found that creates a plan meeting the defined goals. In addition, a user may also select a model to be used together with the defined clinical goals. The model may be a RapidPlan™ model associated with RapidPlan™ (which is a treatment planning tool available at Varian, Palo Alto, Calif.).

Both approaches have different pros and cons. The knowledge based approach may remove the burden of an explicit goal determination, which may be a tedious task and may not be easy to parametrize. However, misjudgments of the training set may occur, and making ad hoc changes to clinical practice may be difficult. The direct clinical goal approach gives a flexible way to change the planning goals, but the explicit goal definition also means that anything that has not been defined as a goal may be treated as ambivalent in the optimization. The knowledge based approach model may be combined with user defined clinical goals in some cases. However, if such combination is not done properly, the clinical practice coded into the knowledge based approach model may not correspond with the explicitly defined goals.

In some embodiments, a treatment planner may combine clinical goals with models for the knowledge based approach (e.g., RapidPlan™ models). In one implementation, clinical goals are used as part of a model definition, adding information to the input data of the knowledge based approach treatment planner (e.g., RapidPlan™ treatment planner). This approach can also train how goals are met in the training set. The treatment planner may also include a predictor configured to predict how the clinical goals are met. In some cases, such treatment planner may also allow selection of training set plans for a particular model, and selection of compatible model, such as RapidPlan™ model.

A treatment planning apparatus includes: a modeler configured to obtain a model definition, wherein the model definition comprises a first quality metric of a first clinical goal; and a treatment planner having: a model trainer configured to obtain a set of existing treatment plans following desired clinical practice, and to perform model training to obtain a trained model based on the existing treatment plans and the first quality metric of the first clinical goal; an objective generator configured to generate a cost function based on the trained model; and an optimizer configured to determine a treatment plan based on the cost function.

Optionally, the model definition does not have a goal value associated with the first quality metric.

Optionally, the treatment planner is configured to determine an estimate of the goal value for the first quality metric.

Optionally, the treatment planner is configured to determine a cost function term based on the estimate of the goal value for the first quality metric.

Optionally, the treatment planner is configured to determine a regression model for principal component of a dose-volume-histogram (DVH) curve.

Optionally, the treatment planner is configured to determine the principal component with emphasis on the DVH curve.

Optionally, the model definition further comprises a first goal value corresponding with the first clinical goal.

Optionally, the treatment planner is configured to determine a cost function term based on the first goal value.

Optionally, the model definition further comprises a second goal value corresponding with the first clinical goal.

Optionally, the model definition further comprises a first weight for the first goal value, and a second weight for the second goal value.

Optionally, the first weight for the first goal value and the second weight for the second goal value are for influencing a manner in which a dose distribution is improved during treatment plan optimization.

Optionally, the model definition further comprises a second quality metric of a second clinical goal.

Optionally, the model definition further comprises a first weight for the first clinical goal, and a second weight for the second clinical goal.

Optionally, the first weight for the first clinical goal and the second weight for the second clinical goal are for prescribing an order in which the first and second clinical goals are to be satisfied during treatment plan optimization.

Optionally, the treatment planner is configured to use machine learning technique to create a statistical model for transferring the desired clinical practice into a new patient geometry, and wherein the objective generator is configured to generate the cost function based on the new patient geometry.

Optionally, the model comprises a Rapidplan™ model.

Optionally, the first quality metric comprises a mean dose, a maximum dose, target coverage, or a relative or absolute volume of an organ having dose larger than a specified dose level.

Optionally, the treatment planner is configured to determine the cost function using a knowledge-based technique based on the set of existing treatment plans and the model definition.

Optionally, the treatment planner is configured to provide a first prediction model for cases where the first clinical goal is met, and a second prediction model for cases where the first clinical goal is not met.

Optionally, the cost function determiner comprises a classifier configured to determine whether a plan would satisfy the first clinical goal or not.

Optionally, the classifier is implemented using decision tree, random forest, or neural network.

A treatment planning method includes: obtaining a model definition by a modeler, wherein the model definition comprises a first quality metric of a first clinical goal; obtaining, by a model trainer, a set of existing treatment plans following desired clinical practice; performing, by the model trainer, model training to obtain a trained model based on the existing treatment plans and the first quality metric of the first clinical goal; generating, by an objective generator, a cost function based on the trained model; and determining a treatment plan based on the cost function.

A product includes a non-transitory medium storing a set of instructions, an execution of which causes a treatment planning method to be performed, the treatment planning method comprising: obtaining a model definition by a modeler, wherein the model definition comprises a first quality metric of a first clinical goal; obtaining, by a model trainer, a set of existing treatment plans following desired clinical practice; performing, by the model trainer, model training to obtain a trained model based on the existing treatment plans and the first quality metric of the first clinical goal; generating, by an objective generator, a cost function based on the trained model; and determining a treatment plan based on the cost function.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
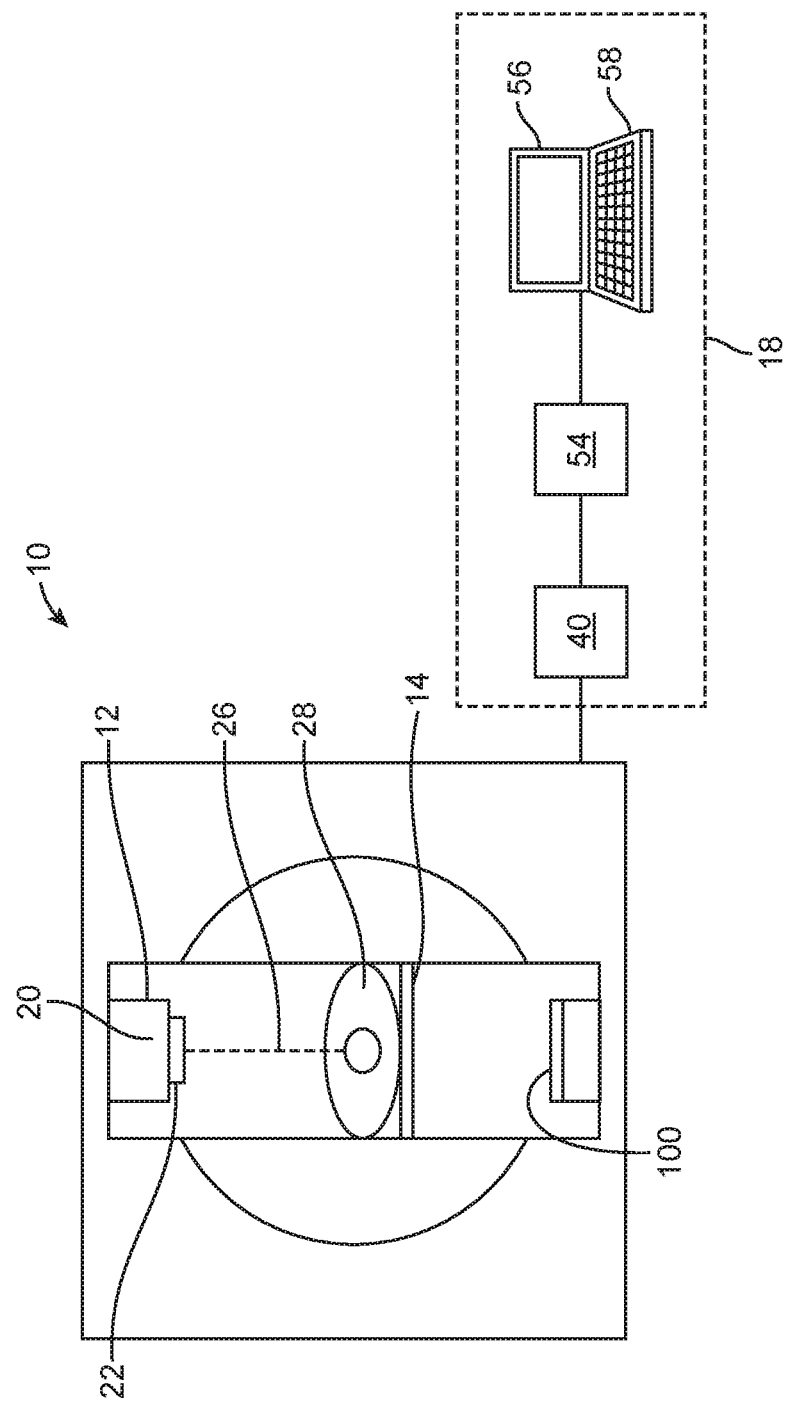
FIG. 1 illustrates a system for delivering radiation in accordance with a treatment plan determined in accordance with embodiments described herein.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

A new treatment planning technique, and apparatus and method implementing such technique, are described herein. The new treatment planning technique combines two treatment planning approaches, i.e., knowledge-based approach, and clinical goal approach, that are fundamentally different.

In the knowledge-based approach, knowledge models are trained by specifying a set of existing treatment plans following a certain desired treatment practice. The idea is that clinical goals are implicitly defined by the dose distributions associated with the existing treatment plans. Thus, the knowledge-based approach obviates the need to explicitly define clinical goals. The role of the dose estimation for a new plan (for a new patient) is to describe the optimal dose distribution under the clinical goals defined implicitly by the training set plans.

In the clinical goal approach, clinical goal may be explicitly defined by a user. A clinical goal may include a quality metric (such as a mean dose of a parotid, or a max dose of the spine) and a goal value. The different goals may have different priorities or weights to tell the treatment planning apparatus how to handle situations where the goals are contradicting each other's (i.e. cannot be satisfied at a same time). There could be also multiple goal values for the same quality metric of a clinical goal with different weights in order to prescribe a desired way a dose distribution is to be improved once the first goal value is reached.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 that projects a beam 26 of radiation towards a patient 28 while the patient 28 is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager, such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. Pat. No. 6,888,919, entitled "RADIO-THERAPY APPARATUS EQUIPPED WITH AN ARTICULABLE GANTRY FOR POSITIONING AN IMAGING UNIT," issued on May 3, 2005, and U.S. Pat. No. 7,649,981, entitled "MULTI-ENERGY X-RAY SOURCE," issued on Jan. 19, 2010. In further embodiments, the radiation source 20 can be a diagnostic radiation source. In the illustrated embodiments, the radiation source 20 is coupled to the arm gantry 12. Alternatively, the radiation source 20 may be located within a bore.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating patient.

Figure 2:
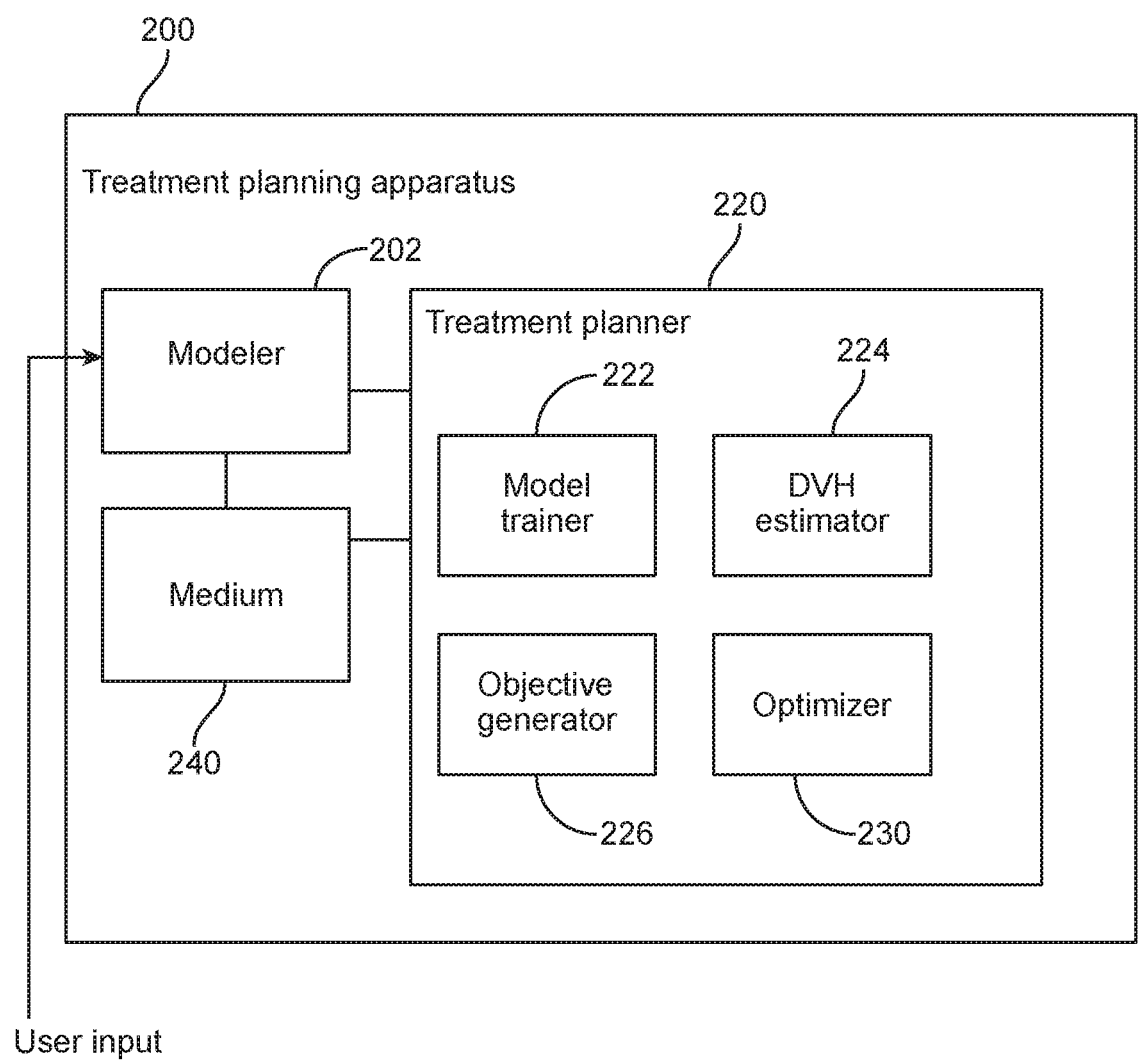
FIG. 2 illustrates an apparatus for determining a treatment plan in accordance with some embodiments.

FIG. 2 illustrates a treatment planning apparatus 200. The treatment planning apparatus 200 may be configured to provide a treatment plan for execution by a treatment machine, such as the one shown in FIG. 1. The treatment planning apparatus 200 includes a modeler 202 configured to obtain a model definition, wherein the model definition comprises a first quality metric of a first clinical goal. The treatment planning apparatus 200 also includes a treatment planner 220 configured to obtain a set of existing treatment plans following desired clinical practice, generate cost function(s) (or objective(s)) based on the set of existing treatment plans and the model definition, and determine a treatment plan based on the cost function(s). As shown in the figure, the treatment planner 220 includes a model trainer 222 configured to train a model to obtain a trained model based on a set of existing treatment plans and the first quality metric of the first clinical goal, a DVH estimator 224 configured to determine a DVH estimate for the subject patient based on the trained model, an objective generator 226 configured to generate cost function(s) for use in treatment planning optimization, and an optimizer 230 configured to perform treatment planning optimization based on the cost function(s) provided by the objective generator 226.

By means of non-limiting examples, the first quality metric may comprise a mean dose, a maximum dose, target coverage, or a relative or absolute volume of an organ having dose larger than a specified dose level.

In other embodiments, the modeler 202 may be configured to obtain additional quality metric(s), such as a second quality metric. The second quality metric may be for the same first clinical goal, or may be for a second clinical goal that is different from the first clinical goal. In such cases, the model trainer 222 may be configured to train a model to obtain a trained model based on a set of existing treatment plans, the first quality metric, and the second quality metric.

In the illustrated embodiments, the treatment planning apparatus 200 also includes a medium 240 storing existing treatment plans. The existing treatment plans include treatment parameters and/or previous models that were developed following desirable clinical practices. In other embodiments, the treatment planning apparatus 200 may not include such medium 240. Instead, the treatment planning apparatus 200 may be configured to communicate with a medium 240 storing the existing treatment plans through a wired or wireless connection. The medium 240 may be a local storage device, a server, a database, etc.

The modeler 202 is configured to obtain user input that defines or affects how a model is to be generated for a new patient. By means of non-limiting examples, the user input may include a selection of certain plan(s) from a list of existing treatment plans, patient geometry, identity of target tissue, identity of organ(s) at risk (OAR(s)), or any combination of the foregoing. In some embodiments, the treatment planning apparatus 200 may provide a user interface for allowing a user to select the plans for model creation. When selecting plan(s), the user may select a subset of plans that represent the current clinical practice, or what the user strives to achieve in the user's clinical practice. In some cases, the modeler 202 may be implemented as a user interface that allows a user to input parameters for model creation and training. By means of non-limiting examples, the input parameters may include quality metrics of clinical goals, selections of existing treatment plans, selection of target tissue, selection of OAR(s), patient geometry, etc., or any combination of the foregoing. In some embodiments, the modeler 202 may provide a data structure for such input parameters.

In some embodiments, the treatment planning apparatus 200 may require a minimum number of plans for model creation. For example, the minimum number of plans required for model creation may be 20. In other cases, the minimum number of plans required may be fewer than 20 (e.g., 15, 10, 5, etc.) or more than 20. However, adding additional plans may help create a more robust model. Models created for certain anatomical regions, such as head and neck, may require more than the minimum number of plans. In some cases, for any structure that a user may want to calculate a DVH estimate, the treatment planning apparatus 200 may require the minimum number of plans containing such structure. For example, for a head and neck model to support the calculation of the estimate of the larynx, at least 20 plans may be required by the treatment planning apparatus 200 that contain an optimized and calculated larynx volume.

In some embodiments, the model definition obtained by the modeler 202 includes the first quality metric for a first clinical goal, but may not have a goal value associated with the first quality metric. For example, a user may specify, via a user interface provided by the treatment planning apparatus 200, that "maximum dose" at spine to be the first quality metric for the first clinical goal, but does not provide any goal value. In such cases, the treatment planner 220 may be configured to determine an estimate of the goal value for the first quality metric by analyzing a set of existing treatment plans retrieved from the medium 240. In one implementation, machine learning may be utilized by the treatment planner 220 to determine the estimate of the goal value for the first quality metric. The treatment planner 220 (e.g., the objective generator 226) may also be configured to determine a cost function term based on the estimate of the goal value for the first quality metric.

In other embodiments, the model definition may include a first quality metric, and a first goal value corresponding with the first clinical goal. For example, the first goal value may be entered by a user via a user interface provided by the treatment planning apparatus 200. In such cases, the treatment planner 220 (e.g., the objective generator 226) may be configured to determine a cost function term based on the first goal value provided by the user.

In some embodiments, in addition to having a first goal value, the model definition may also comprise a second goal value corresponding with the first clinical goal. Optionally, the model definition may further comprise a first weight for the first goal value, and a second weight for the second goal value. The first weight for the first goal value and the second weight for the second goal value are for influencing a manner in which a dose distribution is improved during treatment plan optimization.

Also, in some embodiments, in addition to having a first quality metric, the model definition may further comprise a second quality metric of a second clinical goal. Optionally, the model definition may further include a first weight for the first clinical goal, and a second weight for the second clinical goal. The first weight for the first clinical goal and the second weight for the second clinical goal are for prescribing an order in which the first and second clinical goals are to be satisfied during treatment plan optimization.

In the illustrated embodiments, the treatment planner 220 is configured to perform knowledge-based treatment planning. The treatment planner 220 provides users with models that are representative of clinical practice. These models can be used as baseline for developing radiation treatment plans, such as plans for intensity-modulated radiotherapy (IMRT), volumetric modulated arc therapy (VMAT), etc. The treatment planner 220 takes into account the patient's anatomy and planning objectives to determine estimate of dose-volume-histogram (DVH) for the specific patient. The treatment planner 220 also provides optimization objectives based on each individual patient's critieria.

In particular, the treatment planner 220 is configured to (1) perform plan and patient data modeling (data extraction from clinical database and subsequent model training) using the model trainer 222; (2) estimate DVH(s) for the new patient based on the plan and patient data modeling using the DVH estimator 224, (3) determine optimization objectives (cost functions) based on the estimate DVH(s) using the objective generator 226, and (4) perform optimization based on the optimization objectives using the optimizer 230.

In some embodiments, the model trainer 222 is configured to obtain a number of existing treatment plans from the medium 240, and use these existing treatment plans to train a DVH estimation model. The existing treatment plans may be selected as the ones that have the same OAR structures as those for the new patient. The training of the DVH estimation model generates mathematical parameters (e.g., through principal component analysis and regression models) relating the geometric and dosimetric features, which may then be used by the DVH estimator 224 to estimate DVH for the new patient. Various methodologies may be used by the model trainer 222 to train the DVH estimation model. In one implementation, the model trainer 222 uses an algorithm based on the principles of parametrization of the structure set and dose matrices for the existing treatment plans in the training set. The parameterization identifies the acceptable clinical trade-offs, including the acceptable trade-offs for target coverage and dose to the OARs. The parameterization analyzes the calculated DVH, the distance-to-target histogram (DTH) (which is the relative geometrical relationship between the OAR and planning target volume (PTV)), and the anatomical features (such as, relative overlap volume, relative out-of-field volume, absolute OAR volume, absolute target volume, etc.). Also, in some embodiments, the treatment planning apparatus 200 may use different metric(s) for handling the parts of OAR that are out of field. This approach allows for some aspects of beam geometry to be taken into account. In some cases, potential outliers may be flagged during the model training. The treatment planning apparatus 200 may provide tools to help analyze the outliers and provide recommendations on outlier correction to help determine if edits to the model are required.

In some embodiments, the model is configured by the model trainer 222 from a number of relevant geometric and dosimetric features from a set of selected treatment plans, while taking the quality metric of the clinical goal into account. During the configuration process to configure the model by the model trainer 222, a combination of Principal Component Analysis and regression techniques (PCA-regression) is applied for the in-field region of the OARs, and a mean and standard deviation model for the other OAR regions. The result is a set of model parameters that are generated based on the quality metric of the clinical goal. Although traditional PCA-regression models do not consider quality metrics, various techniques may be employed to makes emphasis (e.g., considers) the certain quality metric(s). In one implementation, a curve may be determined such that the set of curves in the training set are projected to that curve. The projection may then be removed from each member of the set of curves. The size of the remaining curves may be kept as small as possible. In some cases, the size of the remaining curves may be obtained by calculating a norm of the remaining curves, wherein the norm may be altered so that the remaining 'size' of the residual curves is emphasizing the difference in the desired quality metric(s).

After the model parameters are determined, they may then be provided by the model trainer 222 to the DVH estimator 224 for estimating the DVHs for the new patient. Various techniques may be employed to determine the DVH estimate from these model parameters. In some embodiments, the PCA-regression model may be implemented by considering that a DVH may be approximated by a weighted sum of principal components, the weights being the model parameters. So in the estimation process, the regression model is used to give estimates of the principal component weights. The estimated DVH may then be obtained by multiplying each principal component with its corresponding estimated coefficient (or weight) and then summed together.

In some embodiments, the model trainer 222 may be configured to generate and provide a statistical summary about the goodness of the model as an output of the training phase. This serves as a model training evaluation. For example, DVH's principal component average fits may be utilized to indicate the percentage of cases in the training properly reconstructed by the model. Goodness-of-estimation, which may be expressed by mean squared error or chi square, may indicate a difference between the original and the estimated data, and/or a validity of the model (e.g., how probable the model can predict accurately cases not belonging to the training set). A metric may also be provided that measures the distance between the original DVH and the mean of the upper and lower bounds of the estimated DVH.

In some embodiments, in a similar manner, the regression model may be used to provide the confidence interval for the principal components and weights. In order to provide similar confidence interval for the DVH, the variance curve is defined by determining a remaining uncertainty of the regression model dependent parameters (e.g. the principal component weights) and multiplying the point-wise calculated squared principal components by them, and summing them together. By first adding and then subtracting the point-wise calculated square root of that curve, one can determine an estimation for the upper and lower bound DVH.

It should be noted that determining estimates as upper and lower bound is just one example of the many possible implementations, and that other techniques may be used in other embodiments.

After the DVH estimation model is obtained, it may then be applied to a new case (e.g., for a new patient) by the DVH estimator 224 to generate DVH estimates for the organ(s) at risk. In some cases, the DVH estimate(s) may be presented in a form of bands (see FIG. 4). These DVH bands mark the upper and lower bounds that to be achieved by the optimizer 230 during treatment planning optimization. In some embodiments, from the DVH estimation model parameters, the DVH estimator 224 may be configured to generate the most probable upper and lower bound DVHs using the PCA-regression model for the OAR in-field region, and the mean and standard deviation model for the other OAR regions. Note that the mean and standard deviation model is fundamentally the same as the upper and lower bound feature described previously, but here the sub-model is not making any regression analysis (or principal component analysis), and is determining the mean (most probable) and the variance from the training set curves directly. Once the upper and lower bound DVHs are computed, these information may be passed to the objective generator 226 for generating objective(s), e.g., the dose volume constraints (lines and/or points, user definable) for use in the optimization process, according to the choices in the model configuration. At this stage, the user might add further objectives, modify priorities, and perform interactive optimization, if needed. In some embodiments, the objective generator 226 also converts the objectives into cost function (s). In other embodiments, the objective(s) itself may be considered an example of cost function(s).

The objective generator 226 is configured to determine cost function(s) (planning objective(s)) based on the DVH estimate(s). In some embodiments, the objective generator 226 sets target objectives based on prescription and user-defined coverage of the target. In some cases, the objective generator 226 may be configured to determine the optimization objectives and their priorities. Alternative, or additionally, optimization objectives and their priorities may be entered by user via a user interface provided by the treatment planner 220, which are then received by the object generator 226. In some embodiments, Line objective, upper objective, lower objective, mean objective, or any combination of the foregoing, and their respective priorities, may be selected for each structure in the model. In some embodiments, the priorities of optimization objectives may be user configurable per model. The priorities may be manually defined by the user through the user interface of the treatment planning apparatus 200, or may be calculated based on the OAR's DVH estimates and target prescription. The option to include the starting optimization objectives and how the objectives are created is user definable per model.

After the cost function(s) is obtained, the optimizer 230 then performs treatment planning optimization to determine a treatment plan for the new patient based on the cost function(s). The treatment plan may be stored in a non-transitory medium for later use. For example, the treatment plan may be retrieved later, and be executed by a treatment system (such as the system of FIG. 1) for operating the treatment system to deliver treatment radiation to treat the patient.

In some embodiments, the treatment planner 220 is configured to determine a regression model for principal component of a dose-volume-histogram (DVH) curve.

In some embodiments, the treatment planner 220 is configured to determine the principal component with emphasis in the DVH curve.

In some embodiments, the treatment planner 220 is configured to use machine learning technique to create a statistical model for transferring the desired clinical practice into a new patient geometry, and wherein the treatment planner 220 is configured to determine the cost function based on the new patient geometry.

In some embodiments, the treatment planner 220 is configured to determine the cost function using a knowledge-based technique based on the set of existing treatment plans and the model definition.

In some embodiments, the treatment planner 220 is configured to provide a first prediction model for cases where a clinical goal (e.g., target coverage) is met, and a second prediction model for cases where the clinical goal (e.g., target coverage) is not met. Target coverage is merely one of many examples. In other embodiments, the treatment planner 220 may be configured to provide a first prediction model for cases where a clinical goal is met, and a second prediction model for cases where the clinical goal is not met.

In some embodiments, the treatment planner 220 comprises a classifier configured to determine whether a plan would satisfy a clinical goal (e.g., target coverage) goal or not. By means of non-limiting examples, the classifier is implemented using decision tree, random forest, or neural network. In other embodiments, the treatment planner 220 may comprise a classifier configured to determine whether a plan would satisfy a clinical goal or not.

Figure 3:
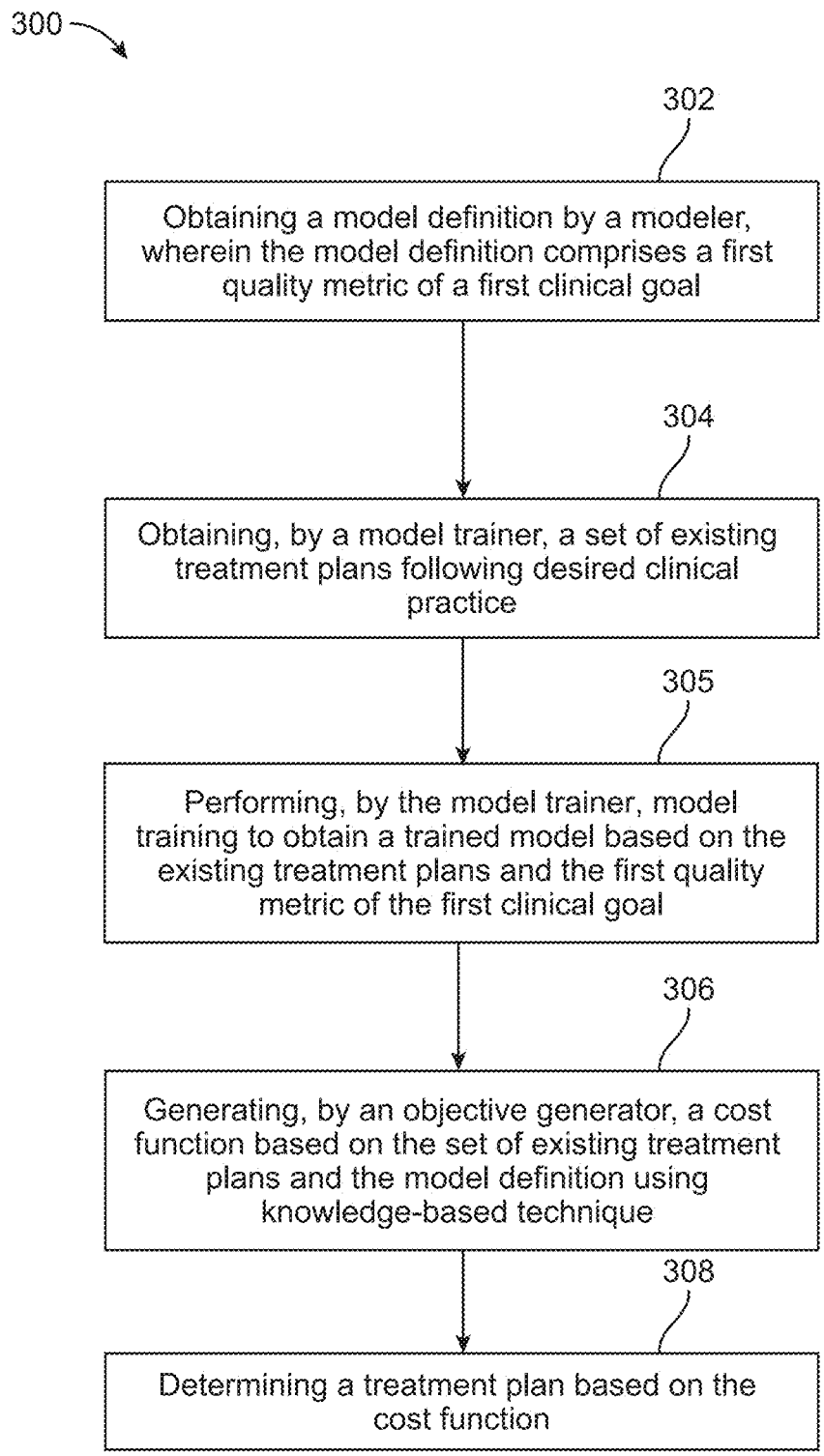
FIG. 3 illustrates a method for determining a treatment plan in accordance with some embodiments.

FIG. 3 illustrates a treatment planning method 300 in accordance with some embodiments. The treatment planning method 300 includes: obtaining a model definition by a modeler, wherein the model definition comprises a first quality metric of a first clinical goal (item 302). The method 300 also includes obtaining, by a model trainer, a set of existing treatment plans following desired clinical practice (item 304). The method 300 also includes performing, by the model trainer, model training to obtain a trained model based on the existing treatment plans and the first quality metric of the first clinical goal (item 305). The method 300 further includes generating, by an objective generator, a cost function based on the trained model (item 306). In some cases, the trained model may be used to determine DVH estimate, and the cost function may be generated based on such DVH estimate. Accordingly, the cost function may be determined based, directly or indirectly, on the trained model. The method 300 also includes determining a treatment plan based on the cost function (item 308).

In some embodiments, a product may be provided for implementing one or more features described herein. The product may include a non-transitory medium storing a set of instructions, an execution of which causes a treatment planning method to be performed. For example, the treatment planning method may be the method 300 of FIG. 3. The treatment planning method may include: obtaining a model definition by a modeler, wherein the model definition comprises a first quality metric of a first clinical goal; obtaining a model definition by a modeler, wherein the model definition comprises a first quality metric of a first clinical goal; obtaining, by a model trainer, a set of existing treatment plans following desired clinical practice; performing, by the model trainer, model training to obtain a trained model based on the existing treatment plans and the first quality metric of the first clinical goal; generating, by an objective generator, a cost function based on the trained model; and determining a treatment plan based on the cost function. Accordingly, in some embodiments, the set of instructions may include instructions for implementing the modeler 202, and instructions for implementing the treatment planner 220. The instructions for implementing the treatment planner 220 may include instructions for implementing the model trainer 222, and instructions for implementing the objective generator 226. In some embodiments, the instructions for implementing the treatment planner 220 may also include instructions for implementing the DVH estimator 224 and/or instructions for implementing the optimizer 230.

Figure 4:
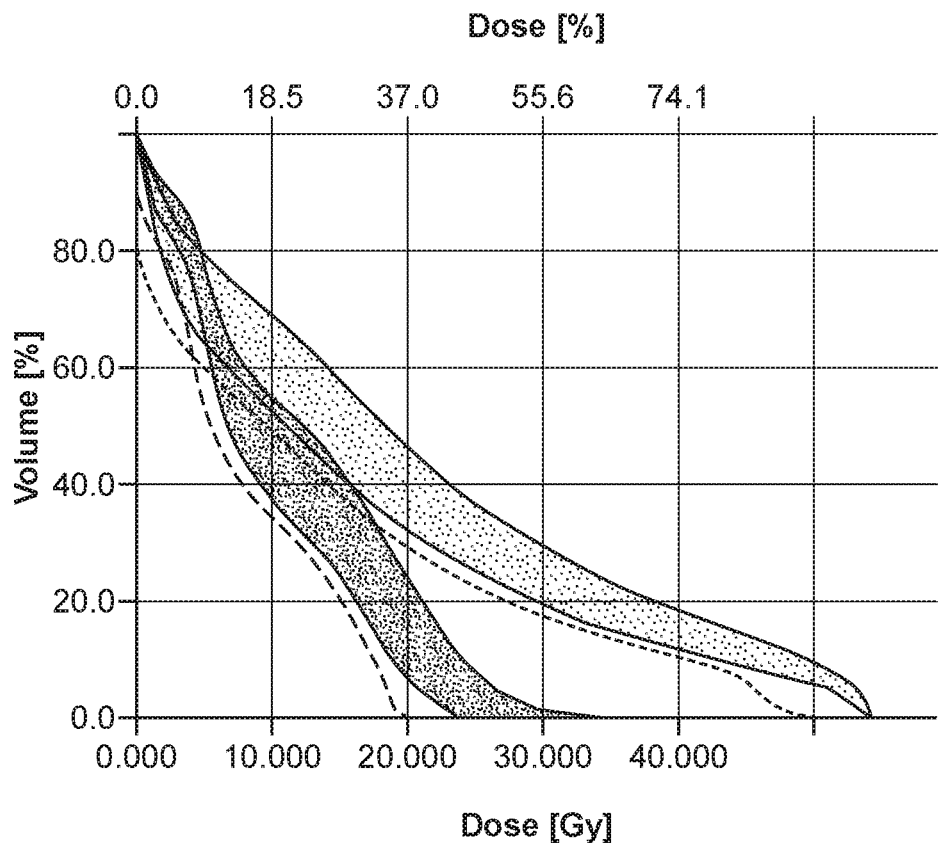
FIG. 4 illustrates an example of DVH.

As discussed, in some embodiments, the DVH estimator 224 of the treatment planner 220 is configured to provide DVH estimate(s). FIG. 4 illustrates examples of DVH estimates that may be generated by the DVH estimator 224. For a new patient, one or more DVH estimates may be provided by the DVH estimator 224. For example, there may be different DVH estimates for different organs of the new patient. Also, in some embodiments, the treatment planning apparatus 200 may be configured to provide the DVH estimates for display on a screen for presentation to the user of the treatment planning apparatus 200.

Figure 5:
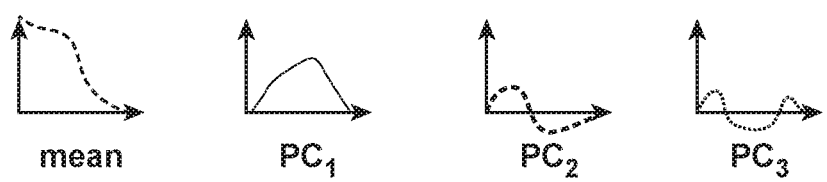
FIG. 5 illustrates examples of principal components of DVHs.

Also as discussed, in some embodiments, the treatment planner 220 is configured to provide principal components of DVHs. FIG. 5 illustrates examples of principal components of DVHs. For a new patient, one or more principal components may be provided by the treatment planning apparatus 200. For example, there may be different principal components of the respective DVHs for different organs of the new patient. Also, in some embodiments, the treatment planning apparatus 200 may be configured to provide the principal components of the DVHs for display on a screen for presentation to the user of the treatment planning apparatus 200.

As discussed, in some embodiments, the model definition may include the relevant quality metrics but no goal values. Even at the absence of goal values, the defined quality metrics may be used to guide the model training to provide estimates for the particular quality metrics directly. For example, if Spine Dmax (maximum dose) is defined as a quality metric, the knowledge model may be trained to provide the estimated Dmax value for Spine. A model predicting directly Dmax for spine is more accurate than reading the Dmax from predicted DVH, which may not have any particular emphasize for the high dose region. In some cases, the built model may emphasize certain region. For example, during the model training by the model trainer 222, a regression model may be created for principal components of the original DVH curves. The principal components may be defined without any particular emphasize in the DVH's. If it is known that for a particular organ the relevant metric is Dmax or V50Gy, it is possible to define the principal component so that it describes the variance of observed DVH set (e.g., especially in the relevant region of the DVH). The treatment planner 220 may provide a regression model that predicts the Partotid gland mean dose or spine max dose (for examples) directly if those have been specified to be the relevant quantity. The clinical goals may also assist the cost function generation. Instead of requiring a user to identify where to put the objectives, the information about the relevant quality metrics may be used to define the objectives to be used in the cost function. Using the spine (and defined relevant quality metric Dmax) as an example, the cost function term related to spine may be selected automatically to be a quadratic function of Dmax with goal value deduced from the estimated Dmax. As other example, if a user has defined V30Gy to be relevant metrics for rectum dose, the model may be applied in treatment planning optimization to generate an objective.

Also, as discussed, in some embodiments, the model definition may include both the relevant quality metrics and the associated goal values (and potentially also the priorities) as the clinical goal. In some embodiments, the training set plans may be evaluated by the model trainer 222 based on whether clinical goals are met. This criterion may be used to cluster the training set plans to sub-classes. The estimation model may be two-phased, with a primary model being a classifier predicting whether a certain goal is met, while each cluster could have its own prediction method to provide estimates for the actual achieved value. For example, a target coverage may have a goal value 95% or higher (portion of the target volume getting the prescribed dose level). Some of the training set plans may have lower coverage, while others may have equal or higher coverage. The model trainer 222 may be configured to train 2 DVH prediction models for all OARs—i.e., a first model for cases where the target coverage is met, and a second model for those cases where the target coverage has not been met. In addition, a third model (a classifier) may be trained to deduce from parameters (such as target volumes, distances to different critical organs, etc.) whether a plan would satisfy the target coverage goal or not. The classifier may be implemented using decision tree, random forest, or deep neural network. Together, these three models may be used to predict DVHs, taking into account that those cases where the goal is reached might differ fundamentally from those where the goal is not reached. When the model is applied, first the classifier is used to predict which sub-model will be used for the actual DVH prediction. In the case of several clinical goals, each goal may have its own classifier, or there could be a single classifier that treats every possible combination of met goals as its own class. In some cases, the priorities of each goal may be considered by the treatment planner 220. In particular, the treatment planner 220 may follow the priorities by trying first to achieve higher priority goal before trying to achieve the lower priority goal. In such cases, the classification may be considered as a branching procedure, where the higher level goal is predicted first and only if met, the classification is continued further to predict if the second level goal is achieved.

One possible implementation of the knowledge based dose estimation algorithm utilizing the clinical goals would be to first provide a supervised learning algorithm for the model trainer 222 to create a model to predict whether the different clinical goals are met or not. This may be done, for example, by a regression model trained using similar geometrical features. The quality metrics may be evaluated for the training set using the accompanying dose matrix, and the achieved value is the dependent parameter. This first step may be omitted in some embodiments, but if it is performed, the formed clustering may be used to divide the training set into subsets where each is used to separately build an estimation model for the dose distribution. The actual values may be predicted using a regression model, with the dependent parameters being the clinical goal values (instead of the principal components of the DVH). The regression model may also use higher priority clinical goal estimates as independent parameters.

The above treatment planning technique is advantageous. This is because combining the clinical goals to a current knowledge based approach would allow the assimilation of different kinds of clinical knowledge more seamlessly. Also, training set based knowledge models are a novel way to describe a desired dose distribution. It does not require explicit definition of acceptable dose distribution, but instead infers them from user given examples. By incorporating clinical goals into the training of the knowledge-based models, and the determination of DVH estimates, it will ensure that the resulting treatment plan will meet such clinical goals.

It should be noted that clinical goal and planning objective are two separate and different things within the context of the embodiments described herein. The primary purpose of the clinical goals is to determine what a good plan should look like, and give guidance for the model trainer 222 to select plan(s) that is better. On the other hand, the primary purpose of the planning objectives is to aid the optimizer 230 to find out a solution (that minimizes the cost function), but does not necessarily guarantee that this optimal solution would be best when evaluated with respect to the clinical goals. In other words, a planning objective is an instruction for the optimizer 230 to construct the cost function so that clinical goals would hopefully be achieved whenever possible (but there is no guarantee that the clinical goals would be met based on such planning objective alone). In some cases, one can combine user-specified objectives to the estimated DVHs to alter how the optimization is done by the optimizer 230. However, in such cases, if the estimated DVHs are not determined based on clinical goals, there is no guarantee that the resulting treatment plan would meet such clinical goals (even though the optimizer performs optimization based on user-defined planning objectives). Accordingly, incorporating clinical goals into the model training is advantageous. By doing so, the clinical goals may guide the model training and the DVH estimation generation. For example, for organ where clinical goals are related to max dose, the estimation can be made (or the accuracy of DVH curves can be emphasized) to the max dose region, thereby improving the accuracy of the estimation of the most relevant quantity.

Also, by incorporating clinical goals in the model training and determination of DVH estimate, it obviates the need or reduces the burden of requiring a user to enter or adjust planning objectives for the optimizer 230. In some cases, after the DVH estimates have been determined, the DVH estimates may be combined with the user given planning objectives. To do so, the user may need to convert the DVH estimates to objectives, combine these objectives with additional ones provided by the user, and define relative weights for these objectives, so that the optimizer can perform treatment planning optimization based on all the planning objectives. This allows experienced user to tweak the optimizer performance, but is confusing for less experienced users. On the other hand, when clinical goals are combined to the DVH estimates in accordance with the embodiments described herein, the DVH estimate may be considered as a more detailed description of how the set of clinical goals should be applied.

Another difference between clinical goals and planning objectives, as they are used in the treatment planning apparatus 200, is that clinical goals are usually defined as prioritized list: i.e., there are clinical goals that are more important to meet than some other clinical goals. On the other hand, the planning objectives have weights which dictate how much individual objectives contribute to the total cost function. Thus, for clinical goals, the priorities define which clinical goals to be pursued, while for planning objectives, the weights dictate how the aversion of different planning objectives are balanced. For example, assuming 'Max dose for spine' is a metric for a clinical goal. There can be different priorities assigned for this metric to achieve different clinical goals. Consider the below examples of clinical goals:

(1) 'It is mandatory that the Max dose for spine is less than 45 Gy'
(2) 'It is preferred that the Max dose for spine is less than 40 Gy'
(3) 'It is beneficial that the Max dose for spine is as low as possible'.

Mathematically, these clinical goals may be expressed as:
(1) $D\_max^Spine<45Gy$ with priority 0
(2) $D\_max^Spine<40$ Gy with priority 1
(3) Minimize $D\_max^Spine$ with priority 2

These clinical goals may be input to the model trainer 222, so that the model trainer 222 can consider these clinical goals when processing the training set of treatment plans to create a model for the new patient. The DVH estimator 224 can then generate DVH estimates based on model parameters (which are based on the clinical goals) output by the model trainer 222.

The same quality metric may also be used for planning objectives, but they are treated very differently by the treatment planning apparatus 200. Consider the below examples of planning objectives:
(1) '$D\_max^Spine<43Gy$ with weight 100'
(2) '$D\_max^Spine<40Gy$ with weight 40'

The above planning objectives may be directly interpreted as quadratic cost function terms:
(1) Cost_spine=100*(max(D_max^Spine−43Gy, 0)^2), or
(2) Cost_spine=40*(max(D_max^Spine−40Gy, 0)^2).
Based on the above planning objectives, the optimizer 230 may then perform optimization by minimizing a total cost function which has contribution from Cost_spine and from various other metrics describing the dose distribution of different critical organs or target structures. However, the above planning objectives are not used by the model trainer 222 to train the estimation model, nor are they incorporated into the DVH estimates generated by the DVH estimator 224.

In some cases, if the solution minimizing the cost function is far from the best when evaluated using the clinical goals, it means that the cost function definition (or one or more planning objectives) is not good. Embodiments described herein solve such practical problem: how to code the clinical goals to planning objectives so that the resulting cost function is meaningful. In the example above, both planning objectives are related to first formulated clinical goal, first being harder (the goal value being only 2 Gy lower than the clinical goal threshold, but the penalty for not reaching the goal being larger). But these two planning objectives will lead to two different plans and it is not guaranteed that the 'optimal plan' will even meet the clinical goal (even though the solution space may contain such plans).

As illustrated above, embodiments of the treatment planning apparatus 200 and the method 300 described herein provide technical improvements in treatment planning devices by making them more accurate in achieving clinical goals. The result is a treatment plan that correctly reflects the desired clinical goals, so that when the treatment plan is executed by a treatment machine, the desired clinical goals will be achieved. This has a practical and concrete impact in the real-world.

Although the above embodiments have been described with reference to delivering treatment radiation that is in the form of x-rays, in other embodiments, the system and technique described herein may be used for other types of treatment energy. For examples, in other embodiments, the radiation source 20 may be a proton source for delivering protons to treat a patient, or an electron source for delivering electrons. Accordingly, embodiments of the treatment planning technique described herein may be used to determine treatment plan for other types of treatment, such as proton treatment.

Also, in one or more embodiments described herein, the modeler 202 and/or the treatment planner 220 may be implemented using hardware, software, or a combination of both. In some cases, the modeler 202 and/or the treatment planner 220 may be one or more modules.

Treatment Planner—Specialized Processing System

Figure 6:
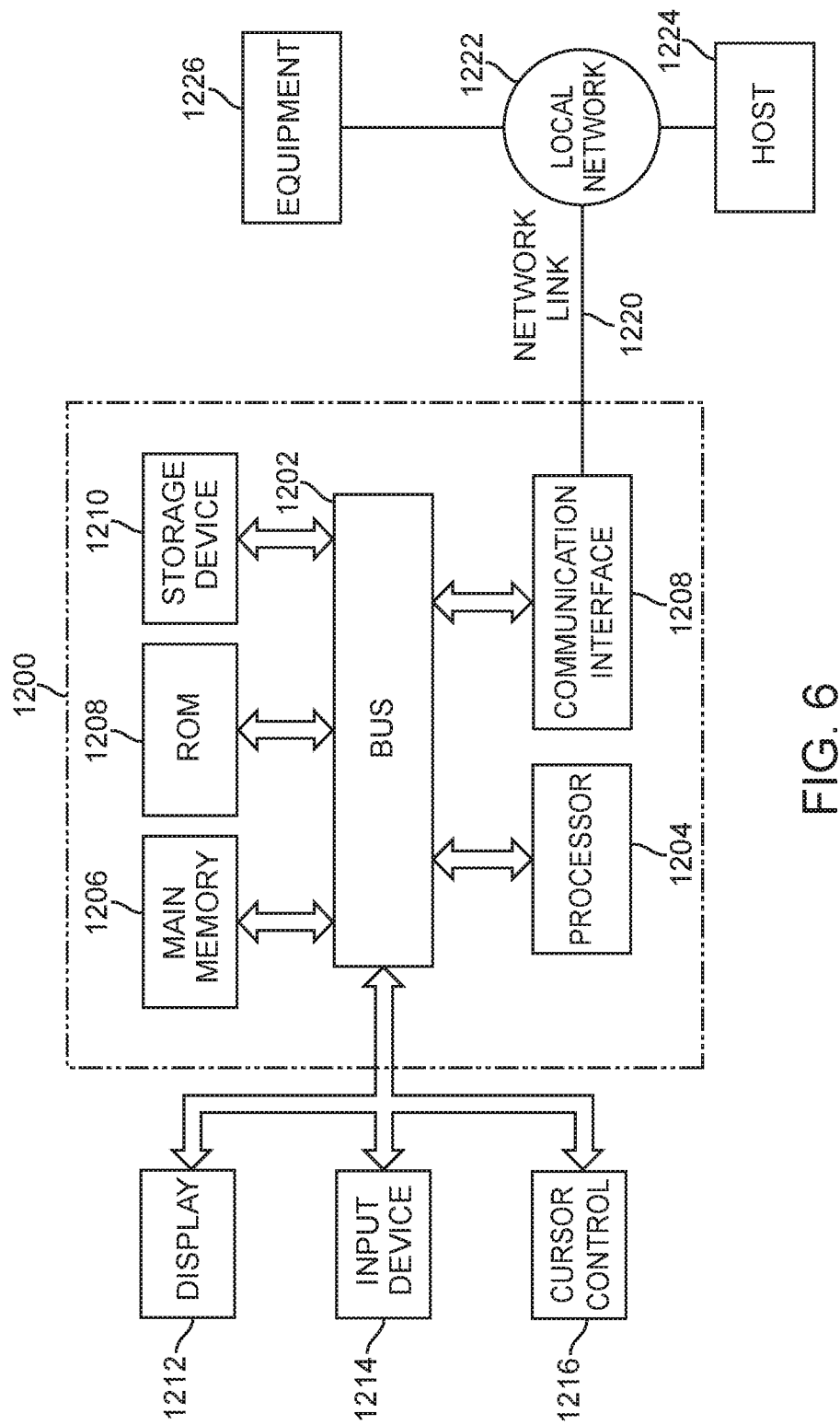
FIG. 6 is a block diagram of a computer system architecture, with which embodiments described herein may be implemented.

FIG. 6 is a block diagram that illustrates an embodiment of a treatment planning apparatus 1200 upon which an embodiment of the invention may be implemented. The treatment planning apparatus 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. The treatment planning apparatus 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The treatment planning apparatus 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The treatment planning apparatus 1200 may be coupled via the bus 1202 to a display 1212, such as a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The treatment planning apparatus 1200 may be used for performing various functions (e.g., calculation) in accordance with the embodiments described herein. According to one embodiment, such use is provided by treatment planning apparatus 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process acts described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Volatile media includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the treatment planning apparatus 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The treatment planning apparatus 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the treatment planning apparatus 1200, are exemplary forms of carrier waves transporting the information. The treatment planning apparatus 1200 can send messages and receive data, including program code, through the network(s), the network link 1220, and the communication interface 1218.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. A treatment planning apparatus, comprising:
   at least one processor; and
   a memory storing computer-executable instructions that, when executed by the at least one processor, cause the treatment planning apparatus to
   obtain a model definition, wherein the model definition includes a first quality metric of a first clinical goal,
   obtain a set of existing treatment plans following desired clinical practice,
   perform model training to obtain a trained model based on the set of existing treatment plans and the first quality metric of the first clinical goal,
   generate a cost function based on the trained model, and
   determine a treatment plan based on the cost function.

2. The apparatus of claim 1, wherein the model definition does not have a goal value associated with the first quality metric.

3. The apparatus of claim 2, wherein the memory stores computer-executable instructions that, when executed by the at least one processor, cause the treatment planning apparatus to determine an estimate of the goal value for the first quality metric.

4. The apparatus of claim 3, wherein the memory stores computer-executable instructions that, when executed by the at least one processor, cause the treatment planning apparatus to determine a cost function term based on the estimate of the goal value for the first quality metric.

5. The apparatus of claim 1, wherein the memory stores computer-executable instructions that, when executed by the at least one processor, cause the treatment planning apparatus to determine a regression model for a principal component of a dose-volume-histogram (DVH) curve.

6. The apparatus of claim 5, wherein the memory stores computer-executable instructions that, when executed by the at least one processor, cause the treatment planning apparatus to determine the principal component with emphasis on the DVH curve.

7. The apparatus of claim 1, wherein the model definition comprises a first goal value corresponding to the first clinical goal.

8. The apparatus of claim 7, wherein the memory stores computer-executable instructions that, when executed by the at least one processor, cause the treatment planning apparatus to determine a cost function term based on the first goal value.

9. The apparatus of claim 7, wherein the model definition comprises a second goal value corresponding to the first clinical goal.

10. The apparatus of claim 9, wherein the model definition comprises a first weight for the first goal value, and a second weight for the second goal value.

11. The apparatus of claim 10, wherein the first weight for the first goal value and the second weight for the second goal value are for influencing a manner in which a dose distribution is improved during treatment plan optimization.

12. The apparatus of claim 1, wherein the model definition comprises a second quality metric of a second clinical goal.

13. The apparatus of claim 12, wherein the model definition comprises:
    a first weight for the first clinical goal, and
    a second weight for the second clinical goal, wherein
    the first weight for the first clinical goal and the second weight for the second clinical goal are for prescribing an order in which the first clinical goal and the second clinical goal are to be satisfied during treatment plan optimization.

14. The apparatus of claim 1, wherein the memory stores computer-executable instructions that, when executed by the at least one processor, cause the treatment planning apparatus to use a machine learning technique to create a statistical model for transferring the desired clinical practice into a patient geometry, and
   generate the cost function based on the patient geometry.

15. The apparatus of claim 1, wherein the first quality metric comprises a mean dose, a maximum dose, target coverage, or a relative or absolute volume of an organ having a dose larger than a specified dose level.

16. The apparatus of claim 1, wherein the memory stores computer-executable instructions that, when executed by the at least one processor, cause the treatment planning apparatus to determine the cost function using a knowledge-based technique based on the set of existing treatment plans and the model definition.

17. The apparatus of claim 1, wherein. the memory stores computer-executable instructions that, when executed by the at least one processor, cause the treatment planning apparatus to provide a first prediction model for cases where the first clinical goal is met, and a second prediction model for cases where the first clinical goal is not met.

18. The apparatus of claim 1, wherein the memory stores computer-executable instructions that, when executed by the at least one processor, cause the treatment planning apparatus to determine whether a plan would satisfy the first clinical goal or not.

19. A treatment planning method, comprising:
- obtaining a model definition by a modeler, wherein the model definition includes a first quality metric of a first clinical goal;
- obtaining, by a model trainer, a set of existing treatment plans following desired clinical practice;
- performing, by the model trainer, model training to obtain a trained model based on the set of existing treatment plans and the first quality metric of the first clinical goal;
- generating, by an objective generator, a cost function based on the trained model; and
- determining a treatment an based on the cost function.

20. A product having a non-transitory medium storing a set of instructions, an execution of which causes a treatment planning method to be performed, the treatment planning method comprising:
- obtaining a model definition by a modeler, wherein the model definition comprises a first quality metric of a first clinical goal;
- obtaining, by a model trainer, a set of existing treatment plans following desired clinical practice;
- performing, by the model trainer, model training to obtain a trained model based on the set of existing treatment plans and the first quality metric of the first clinical goal;
- generating, by an objective generator, a cost function based on the trained model; and
- determining a treatment plan based on the cost function.

* * * * *